United States Patent
Ushiba et al.

(10) Patent No.: US 12,247,950 B2
(45) Date of Patent: Mar. 11, 2025

(54) VIRUS DETECTION SYSTEM, VIRUS DETECTION METHOD, AND VIRUS DETECTION PROGRAM

(71) Applicant: Murata Manufacturing Co., Ltd., Nagaokakyo (JP)

(72) Inventors: Shota Ushiba, Nagaokakyo (JP); Masahiko Kimura, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 971 days.

(21) Appl. No.: 17/236,516

(22) Filed: Apr. 21, 2021

(65) Prior Publication Data

US 2021/0239687 A1    Aug. 5, 2021

Related U.S. Application Data

(63) Continuation of application No. PCT/JP2019/039120, filed on Oct. 3, 2019.

(30) Foreign Application Priority Data

Dec. 4, 2018 (JP) .................... 2018-227533

(51) Int. Cl.
*G01N 27/414* (2006.01)
*G01N 29/06* (2006.01)
*G08C 19/00* (2006.01)
*G01N 33/543* (2006.01)
*G01N 33/569* (2006.01)

(52) U.S. Cl.
CPC ......... *G01N 29/06* (2013.01); *G01N 27/4145* (2013.01); *G08C 19/00* (2013.01); *G01N 33/5438* (2013.01); *G01N 33/56983* (2013.01)

(58) Field of Classification Search
None
See application file for complete search history.

(56) References Cited

U.S. PATENT DOCUMENTS

| | | |
|---|---|---|
| 2003/0143530 A1 | 7/2003 | Klepp et al. |
| 2008/0283875 A1 | 11/2008 | Mukasa et al. |
| 2011/0093249 A1 | 4/2011 | Holmes et al. |
| 2012/0125771 A1 | 5/2012 | Salzer et al. |
| 2015/0309018 A1 | 10/2015 | Goldsmith |
| 2016/0363550 A1 | 12/2016 | Koo et al. |
| 2019/0101507 A1 | 4/2019 | Isogai et al. |

FOREIGN PATENT DOCUMENTS

| | | | |
|---|---|---|---|
| JP | 2002511965 A | 4/2002 | |
| JP | 2004503248 A | 2/2004 | |
| JP | 2005275708 A | 10/2005 | |
| JP | WO 2006/134942 | * 12/2006 | ............ G01N 27/00 |
| JP | 2013050426 A | 3/2013 | |
| JP | 2013508859 A | 3/2013 | |
| JP | 2013544357 A | 12/2013 | |
| JP | 2016047777 A | 4/2016 | |
| JP | 2017514141 A | 6/2017 | |
| WO | 9904043 A1 | 1/1999 | |
| WO | 2006134942 A1 | 12/2006 | |
| WO | 2017183534 A1 | 10/2017 | |

OTHER PUBLICATIONS

International Search Report issued for PCT/JP2019/039120, date of mailing Jan. 7, 2020.
Written Opinion of the International Searching Authority issued for PCT/JP2019/039120, date of mailing Jan. 7, 2020.
"Success in Development of Mobile Genetic Testing Equipment: Bring it to the testing site and detect bacteria and viruses in about 10 minutes", Internet <URL:http://www.nsg.co.jp/~/media/NSG%20JP/ir/Press%20Releases/2017/08Feb2017RapidMobileDNATestingEquipment_J01.pdf>.
"Diagnose influenza in one minute using a smartphone", <URL : http://healthcare-biz.jp/2017/03/%E3%82%A4%E3%83%B3%E3%83%95%E3%83%AB%E3%82%A8%E3%83%B3%E3%82%B6%E3%82%921%E5%88%86%E8%A8%BA%E6%96%AD/>.
"Easy influenza test with tip and app" ;<URL: https://xtech.nikkei.com/dm/atcl/feature/15/060300031/120700015/?ST=health&P=3>; [retrieved Sep. 15, 2021].
https://www.jeri.or.jp/wec/finalist/6th/Sakashita_Risa.html; [retrieved Sep. 15, 2021].

* cited by examiner

*Primary Examiner* — Agnieszka Boesen
(74) *Attorney, Agent, or Firm* — ArentFox Schiff LLP (57) ABSTRACT

A virus detection system is provided for receiving electrical signals that change quantitatively based on an amount of virus, via a communication line, from a measuring device equipped with graphene sensors that output the electrical signals that change quantitatively based on the amount of virus contained in samples collected from subjects and that associate the electrical signals with identification information for each subject. The virus detection further analyzes the amount of the virus contained in the samples collected from each of the subjects based on changes in the electrical signals outputted from the graphene sensors; and sends, via the communication line, analysis results on the amount of virus contained in the samples collected from each of the subjects to the communication terminal pre-registered to each subject.

19 Claims, 8 Drawing Sheets

VIRUS DETECTION SYSTEM, VIRUS DETECTION METHOD, AND VIRUS DETECTION PROGRAM

CROSS REFERENCE TO RELATED APPLICATIONS

The present application is a continuation of PCT/JP2019/039120 filed Oct. 3, 2019, which claims priority to Japanese Patent Application No. 2018-227533, filed Dec. 4, 2018, the entire contents of each of which are incorporated herein by reference.

TECHNICAL FIELD

The present invention relates to a virus detection system, a virus detection method, and a virus detection program.

BACKGROUND

When highly infectious viruses and bacteria such as influenza enter the body of an infected person, they can infect others before the infected person develops symptoms, such as fever, and this is known to spread infections more widely. If infections could be detected before symptoms develop, those suspected of infection could be quarantined before the development of symptoms and the spread of infections could be significantly curtailed. Known technologies for detecting these types of viruses have been disclosed in Patent Documents 1 to 3 and in Non-Patent Documents 4 and 5, identified as follows.

Patent Document 1: JP 2004-503248 A.
Patent Document 2: US 2015/0309018 A1.
Patent Document 3: JP 2013-050426 A.
Non-Patent Document 4: Success in Development of Mobile Genetic Testing Equipment: "Bring it to the testing site and detect bacteria and viruses in about 10 minutes" Internet, available at: http://www.nsg.co.jp/~/media/NSG%20JP/ir/Press%20Releases/2017/08Feb2017RapidMobileD NATestingEquipment_J01.pdf
Non-Patent Document 5: Diagnose influenza in one minute using a smartphone, available at: http://healthcare-biz.jp/2017/03/% E3%82% A4% E3%83% B3% E3%83%95% E3% 83% AB % E3%82% A8% E3%83% B3% E3%82% B6% E3%82%921% E5%88%86% E8% A8% BA % E6%96% AD/

However, the immunochromatography described in Cited Document 1 is not sensitive enough to detect viruses and bacteria before the development of symptoms. While the simple detectors proposed recently in Patent Document 3 and Non-Patent Document 5 make measurements more convenient, the measurement sensitivity of these devices is not sufficient and it can be difficult to detect viruses before symptoms develop. While the technique disclosed in Non-Patent Document 4 can detect viruses before symptoms develop, the equipment is large due to the use of virus cultures and an optical detection method. This makes it difficult to detect viruses quickly and easily in a large number of subjects. While the graphene sensor described in Patent Document 2 can be used to detect viruses quickly and easily with a high degree of sensitivity before symptoms develop, each subject cannot be notified of test results indicating whether they are infected with a virus and the extent of the infection.

SUMMARY OF THE INVENTION

In light of the problems with conventional systems and methodologies, the present invention provides a virus detection system that is constructed to analyze the amount of virus contained in samples collected from a plurality of subjects and notify each subject of the results of the analysis before symptoms develop.

Accordingly, a virus detection system is provided that comprises a measuring device equipped with a plurality of graphene sensors that output electrical signals that change quantitatively based on the amount of virus contained in samples collected from a plurality of subjects; and a computer system connected to the measuring device via a communication line. The computer system is configured to receive via a communication line from the measuring device electrical signals that change quantitatively based on the amount of virus and that are associated with identification information for each subject; analyze the amount of the virus contained in the samples collected from each of the plurality of subjects based on changes in the electrical signals outputted from the plurality of graphene sensors; and transmit, via the communication line, analysis results on the amount of virus contained in the samples collected from each of the plurality of subjects to the communication terminal pre-registered to each subject.

The virus detection system in the present invention is constructed to analyze the amount of virus contained in samples collected from a plurality of subjects and notify each subject of the results of the analysis before symptoms develop.

DETAILED DESCRIPTION OF EMBODIMENTS

Exemplary embodiments of the present invention will now be described with reference to the drawings. Note that components with the same configuration are denoted by the same reference numbers throughout and redundant descriptions of these components have been omitted.

First Exemplary Embodiment

Figure 1:
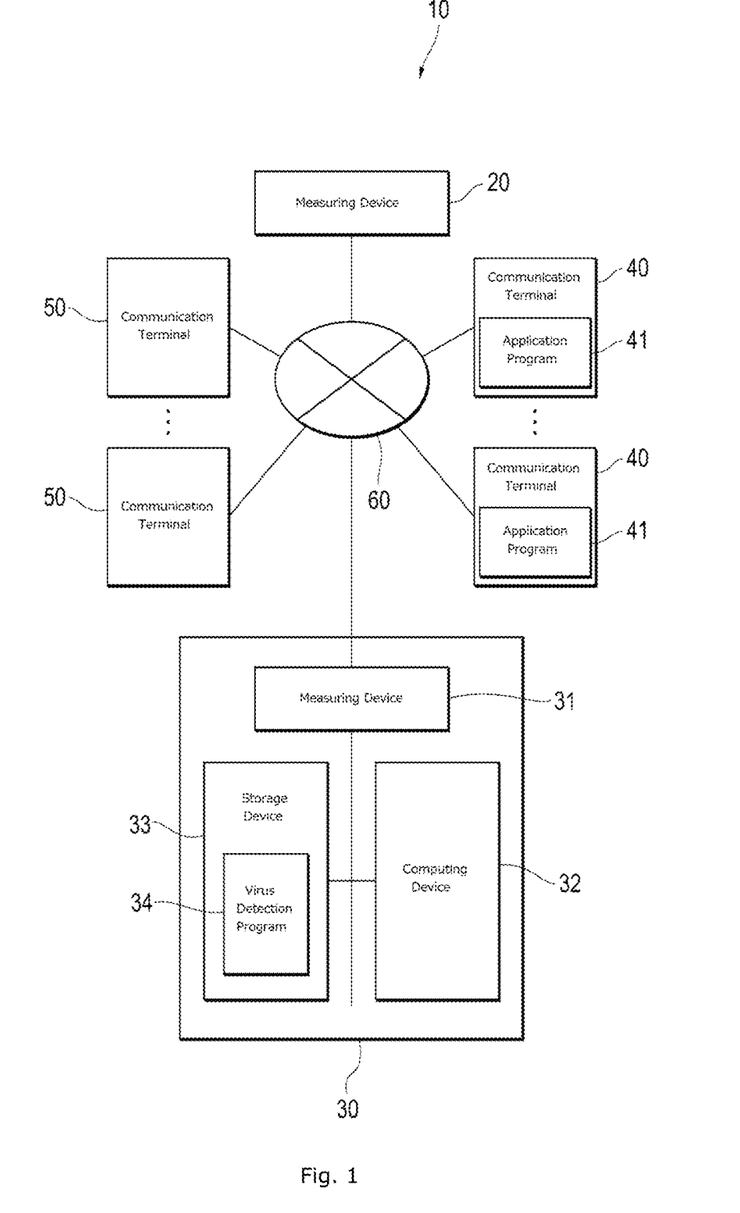
FIG. 1 is a diagram illustrating the hardware configuration of the virus detection system in the first exemplary embodiment.

FIG. 1 is a diagram illustrating the hardware configuration of the virus detection system 10 in the first exemplary embodiment. As shown, the virus detection system 10 comprises a measuring device 20 that quantitatively detects viruses contained in samples (e.g., biological samples such as saliva, exhaled breath, a nasal swab, or nasal discharge) collected from each of a plurality of subjects belonging to a specific group, and a computer system 30 that quantitatively analyzes the extent of a viral infection on a subject basis or group basis based on the detection results of the measuring device 20 and that sends the results of the analysis to pre-registered communication terminals 40, 50. The computer system 30 can be, for example, a host computer or a general-purpose personal computer. The measuring device 20 and the computer system 30 are connected via a wired or wireless communication line 60. The communication line 60 can be, for example, an internet line, mobile communication line, short-range wireless line or the like as would be appreciated to one skilled in the art.

The communication terminals 40 are communication terminals pre-registered to each subject for notifying each subject of the results of the analysis (such as communication terminals used by the subjects themselves or by their parents or guardians). The communication terminals 50 are communication terminals pre-registered to each group for notifying each group of the results of the analysis (such as communication terminals used by those managing the groups). The communication terminals 40, 50 may be, for example, mobile communication terminals such as smartphones, smart watches, and tablets, or personal computers with a communication function for transmitting and/or receiving electronic data and communications. Moreover, an application program 41 is installed in the communication terminals 40 for executing processing in conjunction with the computer system 30 (processing such as retrieving subject identification information and receiving notification of virus analysis results).

The computer system 30 is equipped with a communication device 31 (e.g., a receiver) connected to the measuring device 20 via a communication line 60, a computing device 32, and a storage device 33. The storage device 33 is a computer-readable storage medium such as a disk medium (for example, a magnetic recording medium or an optical magnetic recording medium) or a semiconductor memory (for example, volatile memory or non-volatile memory). This type of recording medium is also known as a non-transient recording medium. This storage device 30 includes a virus detection program 34 (e.g., a virus analyzer), which when executed by a processor of the computer system 30, causes the computer system 30 to execute the virus detection method in the first embodiment. That is, the computing device 32 includes a processor and a main memory, and the virus detection program 34 read from the storage device 32 to the main memory is interpreted and executed by the processor. The virus detection method in the first embodiment will be described in detail later.

For purposes of this disclosure, a "virus" means a virus that has the ability to spread to others via airborne infection or droplet infection. Examples include an influenza virus, rubella virus, enterovirus, or rotavirus.

Figure 2:
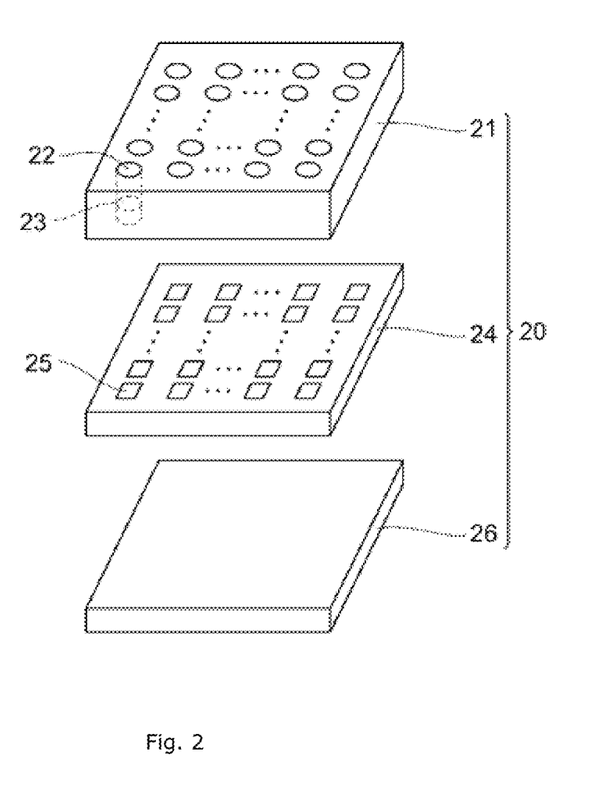
FIG. 2 is a diagram illustrating the configuration of the measuring device in the first exemplary embodiment.

The configuration of the measuring device 20 will now be described with reference to FIG. 2 to FIG. 5. As shown in FIG. 2, the measuring device 20 includes a sample container array 21, a graphene sensor array 24, and a processing circuit 26. The sample container array 21 includes a plurality of sample containers 22 arranged in an array. A filter 23 is provided in each sample container 22 to capture non-virus contaminants. The graphene sensor array 24 includes a plurality of graphene sensors 25 arranged in an array. There is a one-to-one correspondence between sample containers 22 and graphene sensors 25, and each graphene sensor 25 quantitatively detects the viruses in the sample housed inside the corresponding sample container 22. The processing circuit 26 is configured to perform processing, such as authenticating each subject and group and transmitting virus detection results for each subject and group to the computer system 30.

Figure 3:
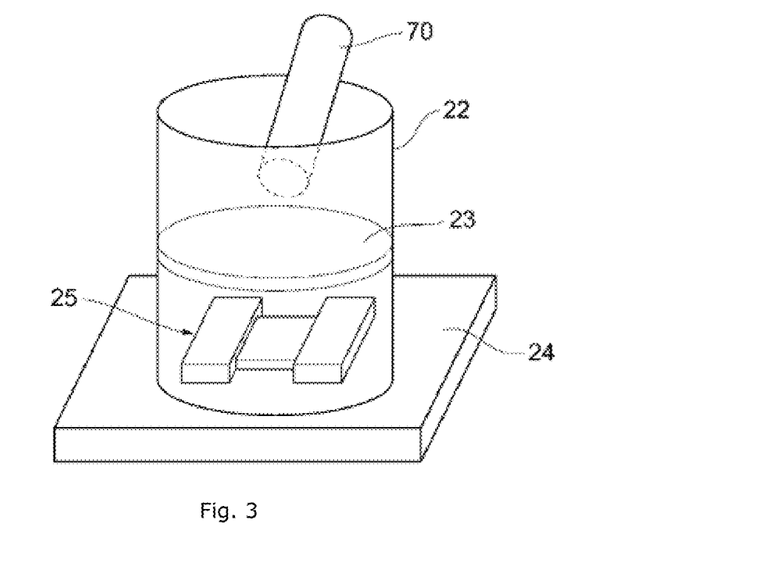
FIG. 3 is a diagram illustrating the measuring device in the first exemplary embodiment.

As shown in FIG. 3, when a sterilized cotton swab 70 containing a sample collected from a subject is inserted into a sample container 22, the non-virus contaminants in the sample included in the sterilized cotton swab 70 are captured by the filter 23. The sample containing the virus with contaminants removed by the filter 23 drips onto the graphene sensor 25. The graphene sensor 25 quantitatively detects the virus in the sample. Cotton can be used as the material in the sterilized cotton swab 70. An example of a sterilized cotton swab 70 that can be used is the Salimetrics Infant's Swab from Salimetrics LLC. In order to prevent accidental ingestion of this type of cotton swab by the subject, saliva may be collected in the subject's mouth on one end of the cotton swab while the collector holds the other end. The amount of saliva collected may be, for example, 1 ml or less.

Figure 4:
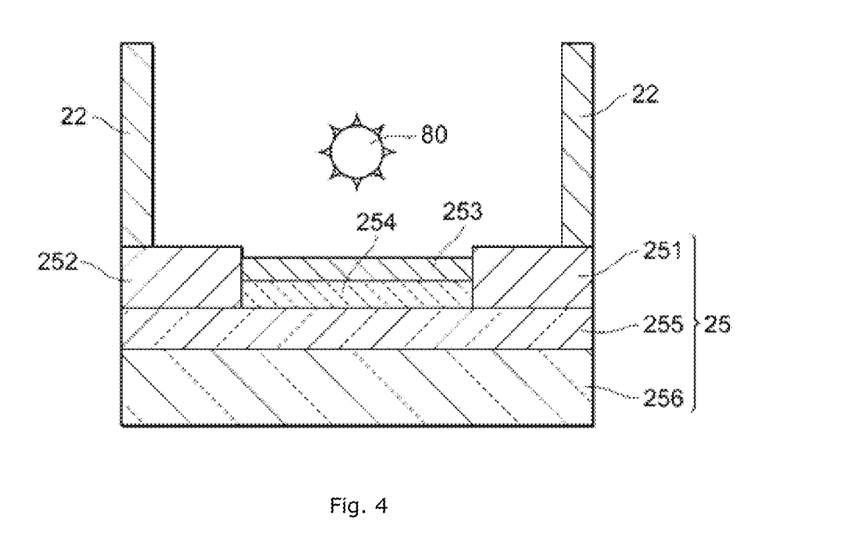
FIG. 4 is a diagram illustrating the configuration of the graphene sensors in the first exemplary embodiment.

As shown in FIG. 4, the graphene sensor 25 includes a drain electrode 251, a source electrode 252, a capturing substance layer 253, graphene 254, silicon dioxide film 255, and a silicon substrate 256. The graphene 254 formed between the drain electrode 251 and the source electrode 252 is laminated with a capturing substance layer 253 that captures the virus 80 in the exemplary aspect. When the virus 80 is captured by the capturing substance layer 253, the electrical characteristics of the graphene sensor 25 (such as the current-voltage characteristics) change in response to the surface charge of the virus 80. The electrical signals (such as the current signals) outputted from the graphene sensor 25 also change in response to changes in the electrical characteristics of the graphene sensor 25. The amount of virus 80 is known to be correlated with the amount of change in the electrical signals. The graphene sensor 25 outputs electrical signals that change quantitatively according to the amount of virus 80 as detection results for the virus 80. Because a graphene sensor array 24 has the ability to detect a virus 80 before the development of symptoms and a plurality of samples can be processed at the same time, it can be configured to analyze the presence and extent of infection with a virus 80 in a plurality of subjects.

According to exemplary aspects, when the virus 80 is an influenza virus, an anti-hemagglutinin antibody or a sialo sugar chain can be used as the capturing substance layer 253. When the virus 80 is a rubella virus, Rubella Virus IgG or Rubella Virus IgM can be used as the capturing substance layer 253. When the virus 80 is an enterovirus, an anti-enterovirus antibody can be used as the capturing substance layer 253. When the virus 80 is a rotavirus, an anti-rotavirus antibody can be used as the capturing substance layer 253. A substance having specific adsorption properties dependent on the type of virus may be used as the capturing substance layer 253.

Figure 5:
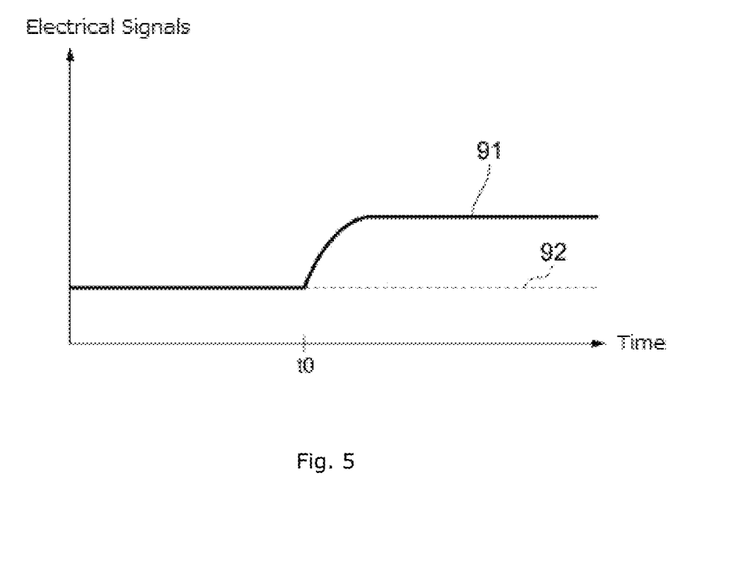
FIG. 5 is a diagram illustrating a change in electrical signals outputted from the graphene sensors in the first exemplary embodiment.

As shown in FIG. 5, the electrical signals outputted from a graphene sensor 25 change depending on whether a virus 80 is present in the sample. The time t0 indicates the time at which the sample was allowed to drip onto the graphene sensor 25. Line 91 indicates the change in electrical signals outputted from the graphene sensor 25 when the virus 80 is present in the sample. Line 92 indicates the electrical signals outputted from the graphene sensor 25 when the virus 80 is not present in the sample. No change is observed in the electrical signals when the virus 80 is not present in the sample. However, the electrical signals change when the virus 80 is present in the sample, and the extent of the change in the electrical samples is greater when the amount of virus 80 present in the sample is larger. Note that used graphene sensors 24 may be discarded after being sterilized, for example, through exposure to ultraviolet rays.

An example of a processing flow for the virus detection method in the first embodiment will now be explained with reference to FIG. 6. A group to which a plurality of subjects belongs may be classified, for example, by organization (such as school, nursery school, or kindergarten) or by facility at which the subjects have gathered (such as a hospital or airport). Subjects do not have to be limited to those who are infected. Among the subjects belonging to a group, some may be infected and others may still be uninfected. In the following example, children belonging to the same kindergarten class are regarded as a specific group, each kindergartner is regarded as a subject, and the extent of infection with a virus 80 is analyzed quantitatively by subject and by group.

In step 601, the measuring device 20 is prepared by a childcare worker who has received instructions on how to use the measuring device 20.

In step 602, the parent or guardian of a subject launches an application program 41 installed in a communication terminal 40. The communication terminal 40 is pre-registered to receive notification of virus analysis results for the subject. When the application program 41 is launched, the communication terminal 40 is connected to the measuring device 20 via, for example, short-range wireless communication.

In step 603, the parent or guardian of the subject captures identification information unique to the subject and identification information on the group (class) to which the subject belongs using the camera in the communication terminal 40, and sends this identification information to the measuring device 20. The identification information unique to the subject or the identification information on the group to which the subject belongs may be, for example, information from a two-dimensional fiducial marker stamped on the name tag of the subject. The identification information unique to the subject may be, for example, a photograph of the subject.

In step 604, the measuring device 20 authenticates the subject based on identification information for the subject and identification information for the group to which the subject belongs received from the communication terminal 40 in step 603.

In step 605, the measuring device 20 assigns the sample container 22 containing the sample collected from the subject authenticated in step 604. In this way, a sample container 22 is individually assigned to each subject so that different sample containers 22 are assigned to contain samples collected from different subjects.

In step 606, the childcare worker puts a sterilized cotton swab 70 in the mouth of the subject and collects saliva from the subject as a sample. The sterilized cotton swab 70 is inserted into the sample container 22 assigned in step 605. In alternative aspects instead of saliva, the sample may be exhaled breath, a nasal swab, or nasal discharge, for example.

In step 607, the measuring device 20 measures the virus contained in the sterilized cotton swab 70 inserted into the sample container 22 in step 606. More specifically, the graphene sensor 25 corresponding to the sample container 22 assigned in step 605 outputs electrical signals that change quantitatively in response to the amount of virus 80 contained in the sterilized cotton swab 70 inserted into the sample container 22 in step 606. Because the time required to measure the virus 80 is, for example, 10 minutes per person and each graphene sensor 25 can conduct a measurement independently of any other graphene sensor 25 that may be conducting a measurement, the waiting time required for a measurement per person is still, for example, about 10 minutes.

In step 608, the measuring device 20 associates the electrical signals that change quantitatively based on the amount of virus 80 to identification information for each subject and identification information for the group to which each subject belongs, and sends the information to the computer system 30 via a communication line 60.

In step 609, the computer system 30 receives (e.g., by a receiver) electrical signals that change quantitatively based on the amount of virus 80 and that have been associated with identification information for each subject and identification information for the group to which each subject belongs from the measuring device 20 via the communication line 60.

In step 610, the computer system 30 analyzes (e.g., by a virus analyzer, such as a program as described herein) the amount of virus 80 contained in the samples collected from each of the subjects based on changes in the electrical signals outputted from each of the graphene sensors 25. Because the relationship between the extent of the change in the electrical signals outputted from a graphene sensor 25 and the amount of virus 80 is known, the computer system 30 quantitatively analyzes the extent of the viral infection on a subject basis based on this known relationship. The computer system 30 quantitatively analyzes the extent of the viral infection not only on a subject basis but on a group basis as well.

In step 611, the computer system 30 sends (e.g., by a transmitter) analysis results on the amount of virus 80 contained in the samples collected from each of the subjects to the communication terminals 40 pre-registered to each subject via a communication line 60. The analysis results on the amount of virus 80 may include the probability of symptoms developing in addition to the amount of virus 80.

In step 612, each communication terminal 40 receives analysis results on the amount of virus 80. The parent or guardian of the subject checks the analysis results on the amount of virus 80 on the communication terminal 40 and, if necessary, takes measures such as sending the subject to the hospital, bringing the subject home, or putting a mask on the subject. The parent or guardian can also estimate the number of days the subject may need to rest based on the amount of virus 80. When the parent or guardian of the subject checks the analysis results on the amount of virus 80 on the communication terminal 40, notification that the results have been read may be sent from the communication terminal 40 to the computer system 30. The computer system 30 may resend analysis results on the amount of virus 80 to a communication terminal 40 if a notification that the results have been read has not been received within a predetermined period of time.

In step 613, the computer system 30 sends the results of an analysis of the extent of infection with the virus 80 on a group basis to communication terminals 50 pre-registered to each group via a communication line 60. The communication terminals 50 can be those used, for example, by the classroom teacher in each kindergarten class. The computer system 30 may also send the results of an analysis of the extent of infection with the virus 80 in each subject in the same class to the communication terminal 50 used by the classroom teacher in the kindergarten class.

In step 614, each communication terminal 50 receives the results of an analysis of the extent of infection with the virus 80 on a group basis. Each communication terminal 50 can be configured to receive the results of an analysis of the extent of infection with the virus 80 on a subject basis in addition to the results of an analysis of the extent of infection with the virus 80 on a group basis. The classroom teacher in each class checks the results of an analysis of the extent of infection with the virus 80 on a subject basis and the results of an analysis on a group basis on the communication terminal 50 and, if necessary, takes measures such as sending subjects to the hospital, sending subjects home, or putting masks on the subjects. The classroom teacher can also take measures such as frequently measuring the body temperature of subjects with a mild infection with the virus 80. The classroom teacher may also have kindergarteners near those suffering from a severe infection with the virus 80 wash their hands and put on a mask. When the classroom teacher checks the analysis results on the amount of virus 80 on the communication terminal 50, notification that the results have been read may be sent from the communication terminal 50 to the computer system 30. The computer system 30 may resend analysis results on the amount of virus 80 to a communication terminal 50 if a notification that the results have been read has not been received within a predetermined period of time.

Figure 7:
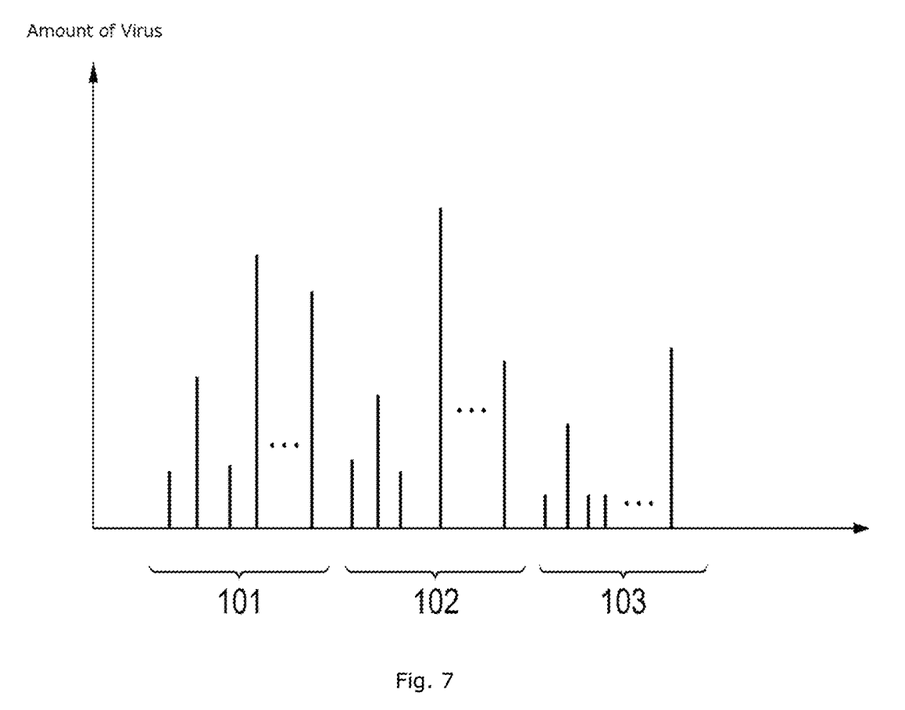
FIG. 7 is a graph showing an example of analysis results from the first embodiment indicating the extent of a viral infection on a group basis.

FIG. 7 is a graph showing an example of analysis results indicating the extent of infection with a virus 80 on a group basis. Here, 101, 102 and 103 indicate the results of an analysis of the amount of virus in a plurality of subjects belonging to different groups (for example, a kindergarten class). A kindergarten manager may decide to send classes home, for example, based on the infection rate in each class. The computer system 30 may also send analysis results indicating the extent of infection with a virus 80 on a group basis to a hospital (e.g., a physician) or the local government. A hospital may, for example, aggregate information on the infection rate with the virus 80 at each kindergarten and prepare vaccines or treatments and treat those infected based on the aggregated results. A local government may issue a notice of an area with a high infection rate based on levels of infection with the virus 80.

By using a substance that has specific adsorption properties dependent on the type of virus 80 as the capturing substance layer 253, a graphene sensor 25 is constructed to detect a virus 80 with a high degree of sensitivity before symptoms develop. Early detection of a virus 80 leads to more appropriate administration of neuraminidase inhibitors and eliminates unnecessary administration of antibacterial drugs. It has also been reported that the appropriate administration of drugs when the level of virus 80 infection is low has the effect of suppressing proliferation of the virus in the body.

In the description provided above, children belonging to the same kindergarten class were regarded as a specific group and each kindergartner was regarded as a subject. However, it should be appreciated that passengers at an airport may be regarded as a specific group, each passenger may be regarded as a subject, and extent of infection with a virus 80 may be analyzed quantitatively by subject and by group. In this case, a member of the airport staff may perform the same actions as the childcare worker, and the passengers or subjects themselves may perform the same actions as the parent or guardians of the kindergartners. The member of the airport staff may take measures commensurate with the risk of infection based on the infection rate among the passengers. For example, members of the airport staff may prevent passengers with a high viral load from boarding aircraft. Members of the airport staff may also oblige passengers with a high probability of developing symptoms to wear a mask. Public health authorities such as the World Health Organization and the US Centers for Disease Control and Prevention report that passengers sitting within two rows of an infected passenger are at high risk of becoming infected themselves. It has been reported in a paper by V. Hertzberg et al. that passengers within one meter of an infected passenger and in an aisle seat are at high risk of becoming infected themselves. Members of the airport staff may take appropriate countermeasures to reduce the risk of infection among passengers based on these reports. Suggested countermeasures for reducing the risk of infection may include changing the seats of infected passengers, changing the seats of children, elderly passengers, and pregnant women away from infected passengers, and requiring passengers near infected passengers to wear masks.

In other examples, residents, outpatients, or staff at a nursing home may be regarded as a specific group, each person in the group may be regarded as a subject, and the extent of infection with a virus 80 may be analyzed quantitatively by subject and by group. Also, residents, outpatients, or staff at a hospital may be regarded as a specific group, each person in the group may be regarded as a subject, and the extent of infection with a virus 80 may be analyzed quantitatively by subject and by group. Also, employees of a company may be regarded as a specific group, each person in the group may be regarded as a subject, and the extent of infection with a virus 80 may be analyzed quantitatively by subject and by group.

The virus detection system 10 in the first exemplary embodiment is configured to analyze the amount of virus 80 in samples collected from each of a plurality of subjects before the development of symptoms and can notify each subject of the results of the analysis. In this way, those suspected of becoming infected can be isolated before symptoms develop and the spread of infection can be significantly reduced. Because the extent of infection with a virus 80 can be analyzed quantitatively on both a subject basis and a group basis, measures can be taken on a group-wide basis to treat the infected and prevent further infection. By using saliva, exhaled breath, a nasal swab, or nasal discharge from each subject as the sample, a virus 80 can be measured easily.

Figure 6:
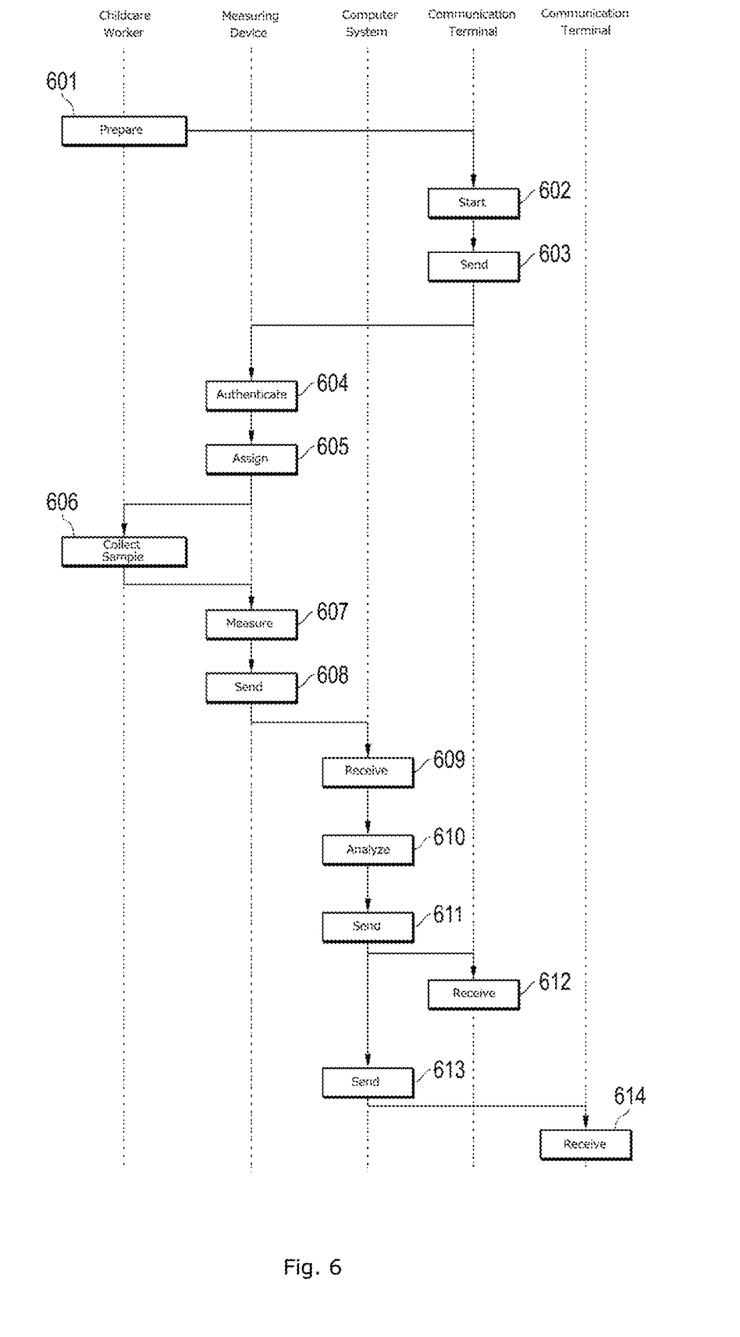
FIG. 6 is a diagram illustrating an example of a processing flow for the virus detection method in the first exemplary embodiment.

The computer system 30 is a system configured to execute the virus detection method described above (e.g., steps 609 to 611 and 613 in FIG. 6, or the receiving step 609, the analyzing step 610, and the sending steps 611 and 613). It is noted that these configurations do not have to be implemented by hardware resources in a computer system 30 working with a virus detection program 34. For example, they can also be implemented by dedicated hardware resources in the computer system 30 (such as an application-specific integrated circuit (ASIC) or a field programmable gate array (FPGA)). The virus detection program 34 may also include software modules for executing the functions and algorithms described herein. In general, the term "module" refers to a real-world device, component, or arrangement of components implemented using hardware, such as by an application specific integrated circuit (ASIC) or field-programmable gate array (FPGA), for example, or as a combination of hardware and software, such as by a microprocessor system and a set of instructions to implement the module's functionality, which (while being executed) transform the microprocessor system into a special-purpose device. A module can also be implemented as a combination of the two, with certain functions facilitated by hardware alone, and other functions facilitated by a combination of hardware and software. In certain implementations, at least a portion, and in some cases, all, of a module can be executed on the processor of a general purpose computer. Accordingly, each module can be realized in a variety of suitable configurations, and should not be limited to any example implementation exemplified herein.

In the description provided above, the apparatus for detecting the virus 80 was a graphene field effect transistor, which is a type of graphene sensor. However, the exemplary aspects of the present invention are not limited to this example. It is noted that any type of graphene sensor can be used. A graphene sensor has a device structure in which electrical characteristics (such as the current-voltage characteristics) change in response to the surface charge of a virus 80, and in which changes in the electrical signals outputted from the graphene sensor (such as current signals or voltage signals) are correlated with the virus 80. A graphene sensor outputs electrical signals that change quantitatively in response to the amount of virus 80 as detection results for a virus 80. Here, the silicon dioxide film 255 and the silicon substrate 256 may be replaced, for example, with a resin substrate or a ceramic substrate. Also, gate voltage may be applied to the graphene 254.

Second Exemplary Embodiment

Figure 8:
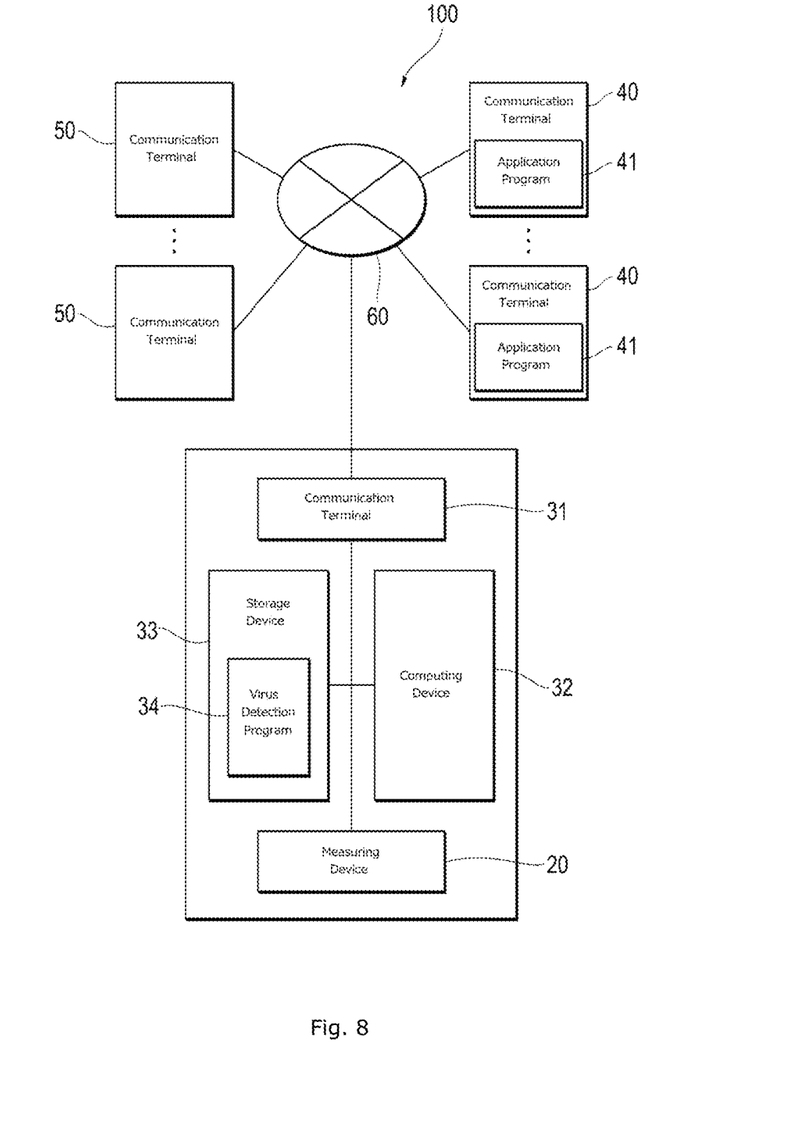
FIG. 8 is a diagram illustrating the hardware configuration of the virus detection system in the second exemplary embodiment.

FIG. 8 is a diagram illustrating the hardware configuration of the virus detection system 100 in a second exemplary embodiment. The first embodiment is a cloud-based system in which the virus 80 is analyzed by a computer system 30 connected to a measuring device 20 via a communication line 60. In contrast, the second embodiment is an on-premises system in which the virus 80 is analyzed by a computer system equipped with a measuring device 20 (i.e., a measuring and analysis system). The differences between the first and second embodiments will now be described. A description of the points of similarities between the two embodiments has been omitted.

The virus detection system 100 is a computer system whose hardware resources include a measuring device 20, a communication device 31, a computing device 32, and a storage device 33. These hardware resources are the same as the measuring device 20, the communication device 31, the computing device 32, and the storage device 33 described in the first exemplary embodiment. The apparatus for detecting the virus 80 can be a graphene field effect transistor, but any type of graphene sensor can be used.

An example of a processing flow for the virus detection method in the second exemplary embodiment will now be explained with reference to FIG. 9. In the following explanation, as in the first embodiment, children belonging to the same kindergarten class are regarded as a specific group, each kindergartner is regarded as a subject, and the extent of infection with a virus 80 is analyzed quantitatively by subject and by group.

In step 901, the measuring device 20 is prepared by a childcare worker who has received instructions on how to use the measuring device 20.

In step 902, the parent or guardian of a subject launches an application program 41 installed in a communication terminal 40. When the application program 41 is launched, the communication terminal 40 is connected to the measuring device 20 via, for example, short-range wireless communication.

In step 903, the parent or guardian of the subject captures identification information unique to the subject and identification information on the group (e.g., a class) to which the subject belongs using the camera in the communication terminal 40, and sends this identification information to the measuring device 20.

In step 904, the measuring device 20 authenticates the subject based on identification information for the subject and identification information for the group to which the subject belongs received from the communication terminal 40 in step 903.

In step 905, the measuring device 20 assigns the sample container 22 containing the sample collected from the subject authenticated in step 904. In this way, a sample container 22 is individually assigned to each subject so that different sample containers 22 are assigned to contain samples collected from different subjects.

In step 906, the childcare worker puts a sterilized cotton swab 70 in the mouth of the subject and collects saliva from the subject as a sample. The sterilized cotton swab 70 is inserted into the sample container 22 assigned in step 905.

In step 907, the measuring device 20 measures the virus contained in the sterilized cotton swab 70 inserted into the sample container 22 in step 906. More specifically, the graphene sensor 25 corresponding to the sample container 22 assigned in step 905 outputs electrical signals that change quantitatively in response to the amount of virus 80 contained in the sterilized cotton swab 70 inserted into the sample container 22 in step 906.

In step 908, the computing device 32 analyzes the amount of virus 80 contained in the samples collected from each of the subjects based on changes in the electrical signals outputted from each of the graphene sensors 25. Because the relationship between the extent of the change in the electrical signals outputted from a graphene sensor 25 and the amount of virus 80 is known, the computing device 32 quantitatively analyzes the extent of the viral infection on a subject basis based on this known relationship. The computing device 32 quantitatively analyzes the extent of the viral infection not only on a subject basis but on a group basis as well.

In step 909, the communication device 31 in response to a command from the computing device 32 sends analysis results on the amount of virus 80 contained in the samples collected from each of the subjects to the communication terminals 40 pre-registered to each subject via a communication line 60. The analysis results on the amount of virus 80 may include the probability of symptoms developing in addition to the amount of virus 80.

In step 910, each communication terminal 40 receives analysis results on the amount of virus 80. When the parent or guardian of the subject checks the analysis results on the amount of virus 80 on the communication terminal 40, notification that the results have been read may be sent from the communication terminal 40 to the virus detection system 100. The virus detection system 100 can resend analysis results on the amount of virus 80 to a communication terminal 40 if a notification that the results have been read has not been received within a predetermined period of time.

In step 911, the communication device 31, in response to a command from the computing device 32, sends the results of an analysis of the extent of infection with the virus 80 on a group basis to communication terminals 50 pre-registered to each group via a communication line 60. The communication device 31 may also send the results of an analysis of the extent of infection with the virus 80 in each subject in the same class to the communication terminal 50 used by the classroom teacher in the kindergarten class.

In step 912, each communication terminal 50 receives the results of an analysis of the extent of infection with the virus 80 on a group basis. Each communication terminal 50 may receive the results of an analysis of the extent of infection with the virus 80 on a subject basis in addition to the results of an analysis of the extent of infection on a group basis. When the classroom teacher checks the analysis results on the amount of virus 80 on the communication terminal 50, notification that the results have been read may be sent from the communication terminal 50 to the virus detection system 100. The virus detection system 100 may resend analysis results on the amount of virus 80 to a communication terminal 50 if a notification that the results have been read has not been received within a predetermined period of time.

Figure 9:
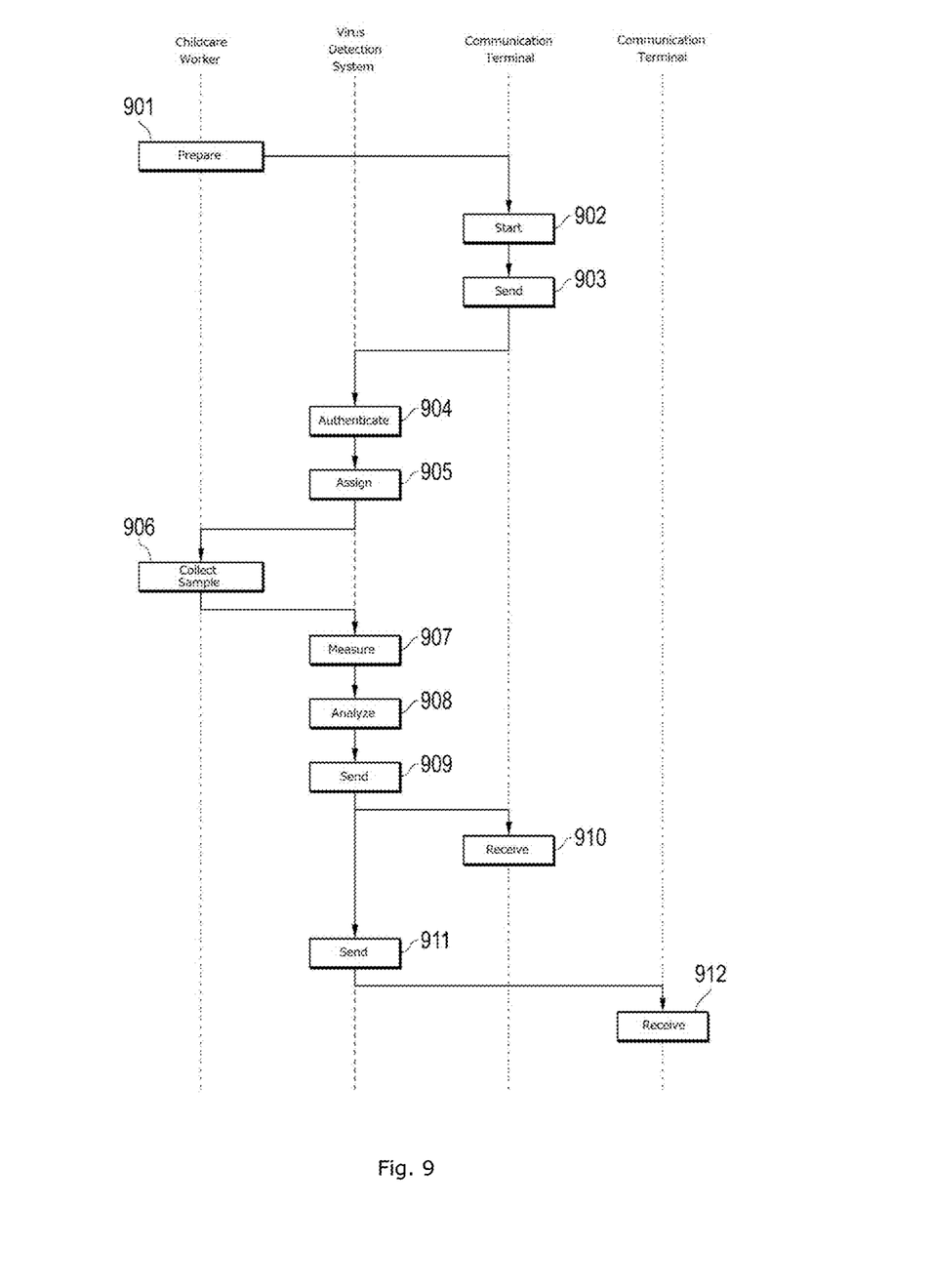
FIG. 9 is a diagram illustrating an example of a processing flow for the virus detection method in the second exemplary embodiment.

According to the exemplary embodiment, the virus detection system 100 is constructed for executing the virus detection method described above (i.e., steps 904, 905, 907, 908, 909 and 911 in FIG. 9, or the authenticating step 904, the assigning step 905, the measuring step 907, the analyzing step 908, and the sending steps 909 and 911). It is noted that these functions do not have to be implemented by hardware resources in a virus detection system 100 working with a virus detection program 34. They may also be implemented by dedicated hardware resources in the virus detection system 100 (such as an application-specific integrated circuit (ASIC) or a field programmable gate array (FPGA)). The virus detection program 34 may also include software modules for performing the functions described herein as noted above.

In general, it is noted that the exemplary embodiments described above are provided to make the present invention easier to understand and not intended to limit interpretation of the present invention. Modifications and improvements can be made without departing from the spirit and scope of the present invention, and the present invention encompasses the equivalent thereof. Those skilled in the art can change the designs of the embodiments where appropriate, and these changes are included in the scope of the present invention as long as they include the characteristics of the present invention. The various elements in the embodiments can be combined as long as they are technically feasible, and these combinations are also included in the scope of the present invention as long as they include the characteristics of the present invention.

REFERENCE SIGNS LIST

10: Virus detection system
20: Measuring device
21: Sample container array
22: Sample container
23: Filter
24: Graphene sensor array
25: Graphene sensor
26: Processing circuit
30: Computer system
31: Communication device
32: Computing device
33: Storage device
34: Virus detection program
40: Communication terminal
41: Application program
50: Communication terminal
60: Communication line
70: Sterilized cotton swab
80: Virus
251: Drain electrode
252: Source electrode
253: Capturing substrate layer
254: Graphene
255: Silicon dioxide film
256: Silicon substrate
100: Virus detection system

The invention claimed is:

1. A virus detection system comprising:
a measuring device having a plurality of graphene sensors constructed to output electrical signals that change quantitatively based on an amount of virus contained in samples collected from a plurality of subjects; and
a computer system connected to the measuring device via a communication line, the computer system comprising:
a receiver configured to receive, via a communication line, the electrical signals from the measuring device and to associate the electrical signals with identification information for each subject of the plurality of subjects,
a virus analyzer configured to analyze the amount of the virus contained in the samples collected from each of the plurality of subjects based on changes in the electrical signals outputted from the plurality of graphene sensors; and
a transmitter configured to send, via the communication line, analysis results based on the amount of virus contained in the samples collected from each of the plurality of subjects to respective communication terminals pre-registered to each subject of the plurality of subjects.

2. The virus detection system according to claim 1,
wherein the plurality of subjects belongs to a defined group, and
wherein the receiver is configured to receives, via a communication line, from the measuring device the electrical signals that change quantitatively based on the amount of the virus and that are associated with the identification information for the defined group to which each of the subjects belongs.

3. The virus detection system according to claim 1,
wherein the virus analyzer is configured to quantitatively analyze an extent of infection with the virus on a group basis, and
wherein the transmitter is configured to send, via the communication line, the analysis results based on the extent of infection with the virus on the group basis to the communication terminal pre-registered to each group.

4. The virus detection system according to claim 1, wherein the samples include at least one of saliva, exhaled breath, a nasal swab, and a nasal discharge from each subject of the plurality of subjects.

5. The virus detection system according to claim 1, wherein the measuring device comprises a plurality of sample containers, a graphene sensor array that includes the plurality of graphene sensors, and a processing circuit for outputting the electrical signals.

6. The virus detection system according to claim 5, wherein each of the plurality of sample containers comprises a filter configured to capture non-virus contaminants.

7. The virus detection system according to claim 1, wherein each of the plurality of graphene sensors includes a drain electrode, a source electrode, a capturing substance layer, graphene disposed below the capturing substance layer, a silicon dioxide film disposed below each of the drain electrode, source electrode and graphene, and a silicon substrate disposed below the silicon dioxide film.

8. The virus detection system according to claim 7, wherein the graphene is disposed between the drain electrode and the source electrode and is laminated with the capturing substance layer to capture the virus.

9. The virus detection system according to claim 8, wherein, when the virus is captured by the capturing substance layer, electrical characteristics of the respective graphene sensor change in response to a surface charge of the virus.

10. The virus detection system according to claim 9, wherein the electrical characteristics comprise a current-voltage characteristics of the respective graphene sensor.

11. A virus detection system comprising:
a plurality of graphene sensors constructed to output electrical signals that change quantitatively based on an amount of virus contained in samples collected from a plurality of subjects;
a virus analyzer configured to analyze the amount of the virus contained in the samples collected from each of the plurality of subjects based on changes in the electrical signals outputted from the plurality of graphene sensors; and
a transmitter configured to send analysis results based on the amount of virus contained in the samples collected from each of the plurality of subjects to respective communication terminals pre-registered to each subject of the plurality of subjects.

12. The virus detection system according to claim 11, further comprising a receiver configured to receive, via the communication line, the electrical signals from the plurality of graphene sensors and to associate the electrical signals with identification information for each subject of the plurality of subjects.

13. The virus detection system according to claim 11,
wherein the plurality of subjects belongs to a defined group,
wherein the virus analyzer quantitatively analyzes an extent of infection with the virus on a group basis, and
wherein the transmitter sends, via the communication line, analysis results on the extent of infection with the virus on the group basis to the communication terminal pre-registered to each group.

14. The virus detection system according to claim 11, wherein the samples include at least one of saliva, exhaled breath, a nasal swab, and a nasal discharge from each subject of the plurality of subjects.

15. The virus detection system according to claim 11, wherein each of the plurality of graphene sensors includes a drain electrode, a source electrode, a capturing substance layer, graphene disposed below the capturing substance layer, a silicon dioxide film disposed below each of the drain electrode, source electrode and graphene, and a silicon substrate disposed below the silicon dioxide film.

16. The virus detection system according to claim 15, wherein the graphene is disposed between the drain electrode and the source electrode and is laminated with the capturing substance layer to capture the virus.

17. The virus detection system according to claim 16, wherein, when the virus is captured by the capturing substance layer, electrical characteristics of the respective graphene sensor change in response to a surface charge of the virus.

18. The virus detection system according to claim 17, wherein the electrical characteristics comprise a current-voltage characteristics of the respective graphene sensor.

19. The virus detection system according to claim 11, further comprising:
a plurality of sample containers;
a graphene sensor array that includes the plurality of graphene sensors, and
a processing circuit for outputting the output electrical signals,
wherein each of the plurality of sample containers comprises a filter configured to capture non-virus contaminants.

* * * * *